(12) United States Patent
Unverricht et al.

(10) Patent No.: US 6,998,504 B1
(45) Date of Patent: Feb. 14, 2006

(54) METHOD FOR THE CATALYTIC GAS PHASE OXIDATION OF PROPENE INTO ACRYLIC ACID

(75) Inventors: Signe Unverricht, Mannheim (DE); Heiko Arnold, Mannheim (DE); Andreas Tenten, Maikammer (DE); Ulrich Hammon, Mannheim (DE); Hans-Peter Neumann, Ludwigshafen (DE); Klaus Harth, Altleiningen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/936,184

(22) PCT Filed: Feb. 28, 2000

(86) PCT No.: PCT/EP00/01631

§ 371 (c)(1),
(2), (4) Date: Sep. 10, 2001

(87) PCT Pub. No.: WO00/53558

PCT Pub. Date: Sep. 14, 2000

(30) Foreign Application Priority Data

| Mar. 10, 1999 | (DE) | 199 10 506 |
| Mar. 10, 1999 | (DE) | 199 10 508 |
| Jun. 17, 1999 | (DE) | 199 27 624 |
| Oct. 6, 1999 | (DE) | 199 48 248 |

(51) Int. Cl.
*C07C 51/16* (2006.01)
*C07C 51/42* (2006.01)

(52) U.S. Cl. ............ 562/545; 562/544; 562/546; 562/600

(58) Field of Classification Search ........ 562/546, 562/545, 600, 544, 598
See application file for complete search history.

(56) References Cited

U.S. PATENT DOCUMENTS

| 2,941,007 | A | * | 6/1960 | Caliahan et al. ............ 568/497 |
| 4,203,906 | A | | 5/1980 | Takada et al. ............... 549/248 |
| 4,298,763 | A | | 11/1981 | Engelbach et al. ......... 568/479 |
| 4,356,783 | A | | 11/1982 | Myklebust et al. .......... 422/197 |
| 4,365,087 | A | | 12/1982 | Kadowaki et al. .......... 562/534 |
| 4,438,217 | A | | 3/1984 | Takata et al. ................ 502/205 |
| 4,499,301 | A | * | 2/1985 | Murib ......................... 562/546 |
| 4,537,874 | A | | 8/1985 | Sato et al. ................... 502/311 |
| 5,198,578 | A | * | 3/1993 | Etzkorn et al. ............. 562/532 |
| 5,198,580 | A | * | 3/1993 | Bartek et al. ............... 562/542 |
| 5,364,825 | A | * | 11/1994 | Neumann et al. .......... 502/311 |
| 5,380,933 | A | * | 1/1995 | Ushikubo et al. ........... 562/549 |
| 5,677,261 | A | | 10/1997 | Tenten et al. ............... 502/439 |
| 5,739,391 | A | * | 4/1998 | Ruppel et al. .............. 562/532 |
| 5,821,390 | A | * | 10/1998 | Ruppel et al. .............. 568/470 |
| 5,855,743 | A | * | 1/1999 | Herbst et al. ............... 203/74 |
| 6,028,220 | A | | 2/2000 | Wada et al. ................. 562/546 |
| 6,395,936 | B1 | | 5/2002 | Arnold et al. |
| 6,403,829 | B1 | | 6/2002 | Unverricht et al. |
| 6,740,779 | B1 | * | 5/2004 | Tenten et al. ............... 562/598 |

FOREIGN PATENT DOCUMENTS

| DE | 25 13 405 | 10/1976 |
| DE | 28 30 765 | 1/1980 |
| DE | 30 02 829 | 7/1980 |
| DE | 33 00 044 | 7/1983 |
| DE | 33 38 380 | 4/1984 |
| DE | 198 55 913 | 6/2000 |
| EP | 0 015 565 | 9/1980 |
| EP | 0 253 409 | 1/1988 |
| EP | 0 257 565 | 3/1988 |
| EP | 0 279 374 | 8/1988 |
| EP | 0 293 224 | 11/1988 |
| EP | 0 450 596 | 10/1991 |
| EP | 0 575 897 | 12/1993 |
| EP | 0 700 893 | 3/1996 |
| EP | 0 714 700 | 6/1996 |
| EP | 0 807 465 | 11/1997 |
| EP | 0 900 774 | 3/1999 |
| JP | 3-294239 | 12/1991 |
| WO | WO 98/24746 | 6/1998 |

OTHER PUBLICATIONS

U.S. Appl. No. 09/936,184, filed Sep. 10, 2001, Unverricht et al.
U.S. Appl. No. 10/806,460, filed Mar. 23, 2004, Dieterle et al.
U.S. Appl. No. 10/912,075, filed Aug. 6, 2004, Schliephake et al.

* cited by examiner

*Primary Examiner*—Cecilia J. Tsang
*Assistant Examiner*—Taylor Victor Oh
(74) *Attorney, Agent, or Firm*—Oblon, Spivak, McClelland, Maier & Neustadt, P.C.

(57) ABSTRACT

A process for the catalytic gas-phase oxidation of propene to acrylic acid, in which the reaction gas starting mixture is oxidized, with a high propene loading, in a first reaction stage, over a first fixed-bed catalyst which is housed in two successive reaction zones A, B, the reaction zone B being kept at a higher temperature than the reaction zone A, and the acrolein-containing product gas mixture of the first reaction stage is then oxidized in a second reaction stage, with a high acrolein loading, over a second fixed-bed catalyst which is housed in two successive reaction zones C, D, the reaction zone D being kept at a higher temperature than the reaction zone C.

31 Claims, No Drawings

METHOD FOR THE CATALYTIC GAS PHASE OXIDATION OF PROPENE INTO ACRYLIC ACID

The present invention relates to a process for the catalytic gas-phase oxidation of propene to acrylic acid, in which a reaction gas starting mixture 1 which contains propene, molecular oxygen and at least one inert gas, comprising at least 20% by volume of molecular nitrogen, and which contains the molecular oxygen and the propene in a molar $O_2:C_3H_6$ ratio of $\geq 1$ is first passed, in a first reaction stage at elevated temperatures, over a first fixed-bed catalyst, whose active material is at least one multimetal oxide containing molybdenum and/or tungsten and bismuth, tellurium, antimony, tin and/or copper, in such a way that the propene conversion in a single pass is $\geq 90$ mol % and the associated selectivity of the acrolein formation and of the acrylic acid byproduct formation together is $\geq 90$ mol %, the temperature of the product gas mixture leaving the first reaction stage is, if required, reduced by direct and/or indirect cooling and, if required, molecular oxygen and/or inert gas are/is added to the product gas mixture, and the product gas mixture, as reaction gas starting mixture 2 which contains acrolein, molecular oxygen and at least one inert gas, comprising at least 20% by volume of molecular nitrogen, and which contains the molecular oxygen and the acrolein in a molar $O_2:C_3H_4O$ ratio of $\geq 0.5$, is then passed, in a second reaction stage at elevated temperatures, over a second fixed-bed catalyst whose active material is at least one molybdenum- and vanadium-containing multimetal oxide, in such a way that the acrolein conversion in a single pass is $\geq 90$ mol % and the selectivity of the acrylic acid formation balanced over both reaction stages is $\geq 80$ mol %, based on propene converted.

The abovementioned process for the catalytic gas-phase oxidation of propene to acrylic acid is generally known (cf. for example DE-A 3002829). In particular, the two reaction stages are known per se (cf. for example EP-A 714700, EP-A 700893, EP-A 15565, DE-C 2830765, DE-C 3338380, JP-A 91/294239, EP-A 807465, WO 98/24746, EP-B 279374, DE-C 2513405, DE-A 3300044, EP-A 575897 and DE-A 19855913).

Acrylic acid is an important monomer which is used as such or in the form of its alkyl esters for producing, for example, polymers suitable as adhesives.

The object of any two-stage fixed-bed gas-phase oxidation of propene to acrylic acid is in principle to achieve a very high space-time yield of acrylic acid ($STY_{Aa}$) (this is the total amount of acrylic acid produced per hour and total volume of the catalyst bed used, in liters, in the case of a continuous process).

There is therefore general interest in carrying out such a two-stage fixed-bed gas-phase oxidation of propene to acrylic acid on the one hand with a very high loading of the first fixed catalyst bed with propene (this is understood as meaning the amount of propene in liters at standard temperature and pressure (=l(S.T.P.); the volume in liters which the corresponding amount of propene would occupy under standard conditions, i.e. at 25° C. and 1 bar) which is passed, as part of the reaction gas starting mixture 1, per hour through one liter of catalyst bed 1) and, on the other hand, with a very high loading of the second fixed catalyst bed with acrolein (this is understood as meaning the amount of acrolein in liters at standard temperature and pressure (=l (S.T.P.); the volume in liters which the corresponding amount of acrolein would occupy under standard conditions, i.e. at 25° C. and 1 bar) which is passed, as part of the reaction gas starting mixture 2, per hour through one liter of catalyst bed 2), without significantly impairing the conversion with respect to propene and acrolein which takes place during a single pass of the reaction gas starting mixture through the two fixed catalyst beds and the selectivity of the associated acrylic acid formation, balanced over both reaction stages (based on propene converted).

The realization of the abovementioned is adversely affected by the fact that both the fixed-bed gas-phase oxidation of propene to acrolein and the fixed-bed gas-phase oxidation of acrolein to acrylic acid on the one hand is highly exothermic and on the other hand is accompanied by a variety of possible simultaneous and subsequent reactions.

With increasing propene or acrolein loading of the respective fixed catalyst bed, in the realization of the intended boundary condition of an essentially constant propene or acrolein conversion, it must therefore be assumed that the selectivity of the formation of desired product decreases as a result of increased heat production (cf. for example EP-B 450 596, Example 1 and Example 2).

The conventional processes for the catalytic fixed-bed gas-phase oxidation of propene to acrolein and of acrolein to acrylic acid, wherein nitrogen is used as a main component of the inert diluent gas and moreover a fixed-bed catalyst present in a reaction zone and homogeneous along this reaction, i.e. having a chemically uniform composition over the fixed catalyst bed, is used, and the temperature of the reaction zone is kept at a value uniform over the reaction zone (temperature of a reaction zone is understood here as meaning the temperature of the fixed catalyst bed present in the reaction zone when the process is carried out in the absence of a chemical reaction; if this temperature inside the reaction zone is not constant, the term temperature of a reaction zone means here the number average of the temperature of the catalyst bed along the reaction zone), therefore limit the applicable propene or acrolein loading of the fixed catalyst bed.

Thus, the propene loading used for the fixed catalyst bed is usually $\leq 155$ l(S.T.P.) of propene/l of catalyst bed·h (cf. for example EP-A 15565 (maximum propene loading=120 l(S.T.P.) of propene/l·h), DE-C 2830765 (maximum propene loading=94.5 l(S.T.P.) of propene/l·h), EP-A 804465 (maximum propene loading=128 l(S.T.P.) of propene/l·h), EP-B 279374 (maximum propene loading=112 l(S.T.P.) of propene/l·h), DE-C 2513405 (maximum propene loading=110 l(S.T.P.) of propene/l·h), DE-A 3300044 (maximum propene loading=112 l(S.T.P.) of propene/l·h), EP-A 575897 (maximum propene loading=120 l(S.T.P.) of propene/l·h), DE-C 3338380 (in essentially all examples, the maximum propene loading is 126 l(S.T.P.) of propene/l·h; only in the case of a special catalyst composition was a propene loading of 162 l(S.T.P.)/l·h realized) and DE-A 19855913 (maximum propene loading=155 l(S.T.P.) of propene/l·h).

WO 98/24746 considers that, at a propene loading of up to 148.8 l(S.T.P.) of propene/l·h, it is necessary to structure the catalyst bed in such a way that its volume-specific activity in the direction of flow of the reaction gas mixture gradually increases.

In an exemplary embodiment with an essentially conventional procedure, JP-A 91/294239 discloses that a propene loading of the catalyst bed of 160 l(S.T.P.) of propene/l·h is possible for a catalytic gas-phase oxidation of propene to acrolein, but only at the expense of a volume-specific activity gradually increasing in the direction of flow of the reaction gas mixture. However, such a procedure is not very practicable on an industrial scale since the gas-phase catalytic oxidation of propene to acrolein is usually carried out in tube-bundle reactors having a few thousand catalyst tubes, each individual one of which has to be loaded with the graded catalyst bed.

In EP-B 450596, a propene loading of the catalyst bed of 202.5 l(S.T.P.) of propene/l·h was realized using a structured catalyst bed in an otherwise conventional procedure. However, this was achieved at the expense of a reduced selectivity with respect to the desired product.

EP-B 253409 and the associated equivalent, EP-B 257565, disclose that the proportion of propene in the reaction gas starting mixture can be increased with the use of an inert diluent gas which has a higher molar heat capacity than molecular nitrogen. Nevertheless, in the two abovementioned publications too, the maximum realized propene loading of the catalyst bed is 140 l(S.T.P.) of propene/l·h.

In EP-A 293224, propene loadings above 160 l(S.T.P.) of propene/l·h were realized but at the expense of a specially used inert diluent gas which is completely free of molecular nitrogen. The disadvantage of this diluent gas is in particular that, in contrast to molecular nitrogen, all its components are desired products which have to be at least partly recycled to the gas-phase oxidation in a complicated manner by reasons of cost-efficiency when the process is carried out continuously.

In a similar manner, the prior art processes limit the applicable acrolein loading of the fixed catalyst bed in a catalytic gas-phase oxidation of acrolein to acrylic acid usually to $\leq 150$ l(S.T.P.) of acrolein/l of catalyst·h (cf. for example EP-B 714700; there, the maximum acrolein loading used=120 l(S.T.P.) of acrolein/l·h).

Two-stage gas-phase oxidations of propene to acrylic acid, in which both a high propene loading and a high acrolein loading of the respective fixed-bed catalyst are used in the two oxidation stages, are virtually unknown from the prior art.

One of the few exceptions is EP-B 253409, cited above, and the associated equivalent EP-B 257565. Nevertheless, in these two publications too, the maximum realized propene loading, in spite of the use of an inert gas having a higher molar heat capacity than nitrogen, and hence essentially automatically also the subsequent acrolein loading of the catalyst bed on direct passage of the product gas mixture of the propene oxidation stage into the acrolein oxidation stage, is $\leq 140$ l(S.T.P.) of reactant (propene or acrolein)/l·h.

It is an object of the present invention to provide a process, as defined at the outset, for the catalytic gas-phase oxidation of propene to acrylic acid, which process ensures a high space-time yield of acrylic acid without having the disadvantages of the high-load procedures of the prior art.

We have found that this object is achieved by a process for the catalytic gas-phase oxidation of propene to acrylic acid, in which a reaction gas starting mixture 1 which contains propene, molecular oxygen and at least one inert gas, comprising at least 20% by volume of molecular nitrogen, and which contains the molecular oxygen and the propene in a molar $O_2:C_3H_6$ ratio of $\geq 1$ is first passed, in a first reaction stage at elevated temperatures, over a first fixed-bed catalyst, whose active material is at least one multimetal oxide containing molybdenum and/or tungsten and bismuth, tellurium, antimony, tin and/or copper, in such a way that the propene conversion in a single pass is $\geq 90$ mol % and the associated selectivity of the acrolein formation and of the acrylic acid byproduct formation together is $\geq 90$ mol %, the temperature of the product gas mixture leaving the first reaction stage is, if required, reduced by indirect and/or direct cooling and, if required, molecular oxygen and/or inert gas are/is added to the product gas mixture, and the product gas mixture, as reaction gas starting mixture 2 which contains acrolein, molecular oxygen and at least one inert gas, comprising at least 20% by volume of molecular nitrogen, and which contains the molecular oxygen and the acrolein in a molar $O_2:C_3H_4O$ ratio of $\geq 0.5$, is then passed, in a second reaction stage at elevated temperatures, over a second fixed-bed catalyst whose active material is at least one molybdenum- and vanadium-containing multimetal oxide, in such a way that the acrolein conversion in a single pass is $\geq 90$ mol % and the selectivity of the acrylic acid formation balanced over both reaction stages is $\geq 80$ mol %, based on propene converted, wherein a) the loading of the first fixed-bed catalyst with the propene contained in reaction gas starting mixture 1 is $\geq 160$ l(S.T.P.) of propene/l of catalyst bed·h, b) the first fixed-bed catalyst consists of a catalyst bed arranged in two spatially successive reacton zones A,B, the temperature of reaction zone A being from 300 to 390° C. or to 350° C. and the temperature of reaction zone B being from 305 to 420° C. or to 380° C. and at the same time at least 5° C. above the temperature of reaction zone A, c) the reaction gas starting mixture 1 flows first through reaction zone A and then through reaction zone B, d) the reaction zone A extends to a propene conversion of from 40 to 80 mol %, e) the loading of the second fixed-bed catalyst with the acrolein contained in reaction gas starting mixture 2 is $\geq 140$ l(S.T.P.) of acrolein/l of catalyst bed·h, f) the second fixed-bed catalyst consists of a catalyst bed arranged in two spatially successive reaction zones C,D, the temperature of reaction zone C being from 230 to 270° C. and the temperature of reaction zone D being from 250 to 300° C. and at the same time at least 5° C. above the temperature of reaction zone A, g) the reaction gas starting mixture 2 flows first through reaction zone C and then through reaction zone D and h) the reaction zone C extends to an acrolein conversion of from 55 to 85 mol %.

Preferably, the reaction zone A extends to a propene conversion of from 50 to 70, particularly preferably from 65 to 75, mol %.

According to the invention, the temperature of reaction zone B is advantageously from 305 to 365° C. or 340° C., particularly advantageously from 310 to 330° C. Furthermore, the temperature of reaction zone B is preferably at least 10° C. above the temperature of reaction zone A.

The higher the chosen propene loading of catalyst bed 1 in the novel process, the greater should be the chosen difference between the temperature of reaction zone A and the temperature of reaction zone B. Usually, however, the abovementioned temperature difference in the novel process is not more 50° C., i.e. the difference between the temperature of reaction zone A and the temperature of reaction zone B may be, according to the invention, up to 20° C., up to 25° C., up to 30° C., up to 40° C., up to 45° C. or up to 50° C.

As a rule, the propene conversion, based on a single pass, in the first reaction stage in the novel process is $\geq 92$ mol % or $\geq 94$ mol %. The selectivity, resulting from a single pass in the first reaction stage, of the acrolein formation and of the acrylic acid byproduct formation is usually $\geq 92$ mol % or $\geq 94$ mol %, frequently $\geq 95$ mol % or $\geq 96$ mol % or $\geq 97$ mol %.

Surprisingly, the abovementioned applies not only in the case of propene loadings of the catalyst bed 1 of $\geq 165$ l(S.T.P.)/l·h or of $\geq 170$ l(S.T.P.)/l·h or $\geq 175$ l(S.T.P.)/l·h or ≧180 l(S.T.P.)/l·h, but also in the case of propene loadings of catalyst bed 1 of ≧185 l(S.T.P.)/l·h or ≧190 l(S.T.P.)/l·h or ≧200 l(S.T.P.)/l·h or ≧210 l(S.T.P.)/l·h and in the case of loadings ≧220 l(S.T.P.)/l·h or ≧230 l(S.T.P.)/l·h or ≧240 l(S.T.P.)/l·h or ≧250 l(S.T.P.)/l·h.

It is surprising that the abovementioned values are achievable even if the inert gas used according to the invention for reaction gas starting mixture 1 comprises ≧30% by volume or ≧40% by volume or ≧50% by volume or ≧60% by volume or ≧70% by volume or ≧80% by volume or ≧90% by volume or ≧95% by volume of molecular nitrogen.

In the case of propene loadings of catalyst bed 1 above 250 l(S.T.P.)/1-h, the presence of inert diluent gases such as propane, ethane, methane, pentane, butane, $CO_2$, CO, steam and/or noble gases (here, inert diluent gases should generally be those which undergo less than 5%, preferably less than 2%, conversion during a single pass through the respective reaction stage) is recommended for reaction gas starting mixture 1 for the novel process. Of course, these gases and their mixtures can however also be present in reaction gas starting mixture 1 at lower propene loadings of catalyst bed 1 or can be used as sole diluent gases. It is surprising that the novel process can be carried out using a catalyst bed 1 which is homogeneous, i.e. chemically uniform, when considered over the reaction zones A, B, without suffering significantly from reduced conversions and/or selectivities.

In the novel process, the propene loading of the first fixed-bed catalyst usually does not exceed 600 l(S.T.P.)/l·h. Typically, the propene loadings of the first fixed-bed catalyst in the novel process, without significant reduction of conversion and selectivity, are ≦300 l(S.T.P.)/l·h, frequently ≦250 l(S.T.P.)/l·h.

In the novel process, the operating pressure in the first reaction stage may be below atmospheric pressure (e.g. up to 0.5 bar) or above atmospheric pressure. Typically, the operating pressure in the first reaction stage is from 1 to 5, frequently from 1.5 to 3.5, bar. Usually, the reaction pressure in the first reaction stage does not exceed 100 bar.

According to the invention, the molar $O_2:C_3H_6$ ratio in the reaction gas starting mixture 1 must be ≧1. Usually, this ratio is ≦3. Frequently, the molar $O_2:C_3H_6$ ratio in the reaction gas starting mixture 1 is, according to the invention, ≧1.5 and ≦2.0.

A suitable source of the molecular oxygen required in the first reaction stage is air, as well as air depleted in molecular nitrogen (e.g. ≧90% by volume of $O_2$, ≦10% by volume of $N_2$).

According to the invention, the proportion of propene in reaction gas starting mixture 1 may be, for example, from 4 to 15, frequently from 5 to 12, % by volume or from 5 to 8% by volume (based in each case on the total volume).

The novel process is frequently carried out at a volume ratio of propene to oxygen to inert gases (including steam) in the reaction gas starting mixture 1 of 1:(1.0 to 3.0):(5 to 25), preferably 1:(1.7 to 2,3):(10 to 15).

As a rule, the reaction gas starting mixture 1 contains essentially no further components apart from said constituents.

Suitable fixed-bed catalysts 1 for the novel process are all those whose active material is at least one Mo-, Bi- and Fe-containing multimetal oxide.

This means that in principle all those catalysts which are disclosed in DE-C 3338380, DE-A 19902562, EP-A 15565, DE-C 2380765, EP-A 807465, EP-A 279374, DE-A 3300044, EP-A 575897, U.S. Pat. No. 4,438,217, DE-A 19855913, WO 98/24746, DE-A 19746210 (those of the formula II), JP-A 91/294239, EP-A 293224 and EP-A 700714 can be used as fixed-bed catalysts 1. This applies in particular to the exemplary embodiments in these publications, among which those of EP-A 15565, of EP-A 575897, of DE-A 19746210 and of DE-A 19855913 are particularly preferred. Particularly noteworthy in this context are a catalyst according to Example 1c of EP-A 15565 and a catalyst which is to be prepared in a corresponding manner but as active material has the composition $Mo_{12}Ni_{6.5}Zn_2Fe_2Bi_1P_{0.0065}K_{0.06}O_x \cdot 10SiO_2$. Also noteworthy are the example with the consecutive No. 3 from DE-A 19855913 (stoichiometry: $Mo_{12}Co_7Fe_3Bi_{0.6}K_{0.08}Si_{1.6}O_x$) as an unsupported hollow cylindrical catalyst measuring 5 mm×3 mm×2 mm (external diameter×height×internal diameter) and the unsupported catalyst comprising multimetal oxide II and according to Example 1 of DE-A 19746210. Further possible examples are the multimetal oxide catalysts of U.S. Pat. No. 4,438,217. The latter is true in particular when these hollow cylinders measure 5 mm×2 mm×2 mm, or 5 mm×3 mm×2 mm, or 6 mm×3 mm×3 mm, or 7 mm×3 mm×4 mm (in each case external diameter×height×internal diameter).

A large number of the multimetal oxide active materials suitable as fixed-bed catalysts 1 can be subsumed under the formula I $$Mo_{12}Bi_aFe_bX^1_cX^2_dX^3_eX^4_fO_n, \quad \text{(I)}$$

where
X¹ is nickel and/or cobalt,
x² is thallium, an alkali metal and/or an alkaline earth metal,
X³ is zinc, phosphorus, arsenic, boron, antimony, tin, cerium, lead and/or tungsten,
X⁴ is silicon, aluminum, titanium and/or zirconium,
a is from 0.5 to 5,
b is from 0.01 to 5, preferably from 2 to 4,
c is from 0 to 10, preferably from 3 to 10,
d is from 0 to 2, preferably from 0.02 to 2,
e is from 0 to 8, preferably from 0 to 5,
f is from 0 to 10 and
n is a number which is determined by the valency and frequency of the elements other than oxygen in I.

They are obtainable in a manner known per se (cf. for example DE-A 4023239) and are usually shaped as such into spheres, rings or cylinders or used in the form of coated catalysts, i.e. preshaped, inert supports coated with the active material. However, they can of course also be used in powder form as catalysts 1. According to the invention, the multimetal oxide catalyst ACS-4 comprising Bi, Mo and Fe, from Nippon Shokubai, can of course also be used as catalyst 1.

In principle, active materials, in particular those of the formula I, which are suitable for the fixed-bed catalysts 1 are prepared in a simple manner by producing, from suitable sources of their elemental constituents, a very intimate, preferably finely divided dry blend having a composition corresponding to their stoichiometry, and calcining said dry blend at from 350 to 650° C. The calcination can be effected either under inert gas or under an oxidizing atmosphere, e.g. air (mixture of inert gas and oxygen) or under reducing atmosphere (e.g. mixture of inert gas, $NH_3$, CO and/or $H_2$). The duration of calcination may be from a few minutes to a few hours and usually decreases with the temperature. Suitable sources of the elemental constituents of the multimetal oxide active materials I are those compounds which are already oxides and/or those compounds which can be converted into oxides by heating, at least in the presence of oxygen.

In addition to the oxides, particularly suitable starting compounds are halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate, which decompose and/or can be decomposed, at the latest during the subsequent calcination, into compounds which escape completely in gaseous form, can additionally be incorporated into the intimate dry blend).

The thorough mixing of the starting compounds for the preparation of multimetal oxide materials I can be effected in dry or in wet form. If it is effected in dry form, the starting compounds are expediently used as finely divided powders and, after mixing and, if required, compaction, are subjected to calcination. However, the thorough mixing is preferably effected in wet form. Usually, the starting compounds are mixed with one another in the form of an aqueous solution and/or suspension. Particularly intimate dry blends are obtained in the mixing process described when exclusively dissolved sources of the elemental constituents are used as starting material. The preferably used solvent is water. The aqueous material obtained is then dried, the drying process preferably being effected by spray drying the aqueous mixture at outlet temperatures of from 100 to 150° C.

The multimetal oxide materials suitable as novel fixed-bed catalysts 1, in particular those of the formula I, can be used for the novel process both in powder form and after shaping to specific catalyst geometries, it being possible to carry out the shaping before or after the final calcination. For example, unsupported catalysts can be prepared from the powder form of the active material or its uncalcined and/or partially calcined precursor material by compaction to give the desired catalyst geometry (for example by pelleting or extrusion), it being possible, if required, to add assistants, such as graphite or stearic acid as lubricants and/or molding assistants and reinforcing agents, such as microfibers of glass, asbestos, silicon carbide or potassium titanate. Suitable geometries for unsupported catalysts are, for example, solid cylinders or hollow cylinders having an external diameter and a length of from 2 to 10 mm. In the case of the hollow cylinders, a wall thickness of from 1 to 3 mm is expedient. The unsupport catalyst may of course also have a spherical geometry, it being possible for the sphere diameter to be from 2 to 10 mm.

Of course, the shaping of the pulverulent active material or of its pulverulent precursor material which has not yet been calcined and/or has been partially calcined can also be carried out by application to preshaped inert catalyst supports. Coating of the supports for the preparation of the coated catalysts is carried out as a rule in a suitable rotatable container, as disclosed, for example, in DE-A 2909671, EP-A 293859 or EP-A 714700. For coating of supports, the powder material to be applied is expediently moistened and is dried again after application, for example by means of hot air. The coat thickness of the powder material applied to the support is expediently chosen to be in the range from 10 to 1000 µm, preferably from 50 to 500 µm, particularly preferably from 150 to 250 µm.

Suitable support materials are conventional porous or nonporous aluminas, silica, thorium dioxide, zirconium dioxide, silicon carbide or silicates, such as magnesium silicate or aluminum silicate. The supports may have a regular or irregular shape, those having a regular shape with pronounced surface roughness, for example spheres or hollow cylinders, being preferred. The use of essentially nonporous, spherical steatite supports which have a rough surface and whose diameter is from 1 to 8 mm, preferably from 4 to 5 mm, is suitable. However, the use of cylinders whose length is from 2 to 10 mm and whose external diameter is from 4 to 10 mm as supports is also suitable. Where the supports are rings suitable according to the invention, the wall thickness is moreover from 1 to 4 mm. Annular supports preferably to be used according to the invention have a length of from 3 to 6 mm, an external diameter of from 4 to 8 mm and a wall thickness of from 1 to 2 mm. According to the invention, rings measuring 7 mm×3 mm×4 mm (external diameter×length×internal diameter) are also particularly suitable as supports. The fineness of the catalytically active oxide materials to be applied to the surface of the support is of course adapted to the desired coat thickness (cf. EP-A 714 700).

Advantageous multimetal oxide active materials to be used according to the invention as fixed-bed catalysts 1 are furthermore materials of the formula II

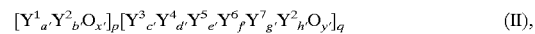  (II), where $y^1$ is bismuth, tellurium, antimony, tin and/or copper,
$y^2$ is molybdenum and/or tungsten,
$y^3$ is an alkali metal, thallium and/or samarium,
$y^4$ is an alkaline earth metal, nickel, cobalt, copper, manganese, zinc, tin, cadmium and/or mercury,
$y^5$ is iron, chromium, cerium and/or vanadium,
$y^6$ is phosphorus, arsenic, boron and/or antimony,
$y^7$ is a rare earth metal, titanium, zirconium, niobium, tantalum, rhenium, ruthenium, rhodium, silver, gold, aluminum, gallium, indium, silicon, germanium, lead, thorium and/or uranium,
a' is from 0.01 to 8,
b' is from 0.1 to 30,
c' is from 0 to 4,
d' is from 0 to 20,
e' is from 0 to 20,
f' is from 0 to 6,
g' is from 0 to 15,
h' is from 8 to 16,
x',y' are numbers which are determined by the valency and frequency of the elements other than oxygen in II and
p,q are numbers whose ratio p/q is from 0.1 to 10, containing three-dimensional regions which are delimited from their local environment as a result of their composition differing from their local environment and have the chemical composition $Y^1_{a'}Y^2_{b'}O_{x'}$ and whose maximum diameter (longest line passing through the center of gravity of the region and connecting two points present on the surface (interface) of the region) is from 1 nm to 100 µm, frequently from 10 nm to 500 nm or from 1 µm to 50 or 25 µm.

Particularly advantageous novel multimetal oxide materials II are those in which $y^1$ is bismuth.

Preferred among these in turn are those of the formula III

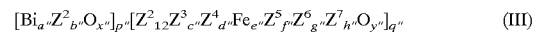  (III)

where $Z^2$ is molybdenum and/or tungsten,
$Z^3$ is nickel and/or cobalt,
$Z^4$ is thallium, an alkali metal and/or an alkaline earth metal,
$Z^5$ is phosphorus, arsenic, boron, antimony, tin, cerium and/or lead,
$Z^6$ is silicon, aluminum, titanium and/or zirconium, $Z^7$ is copper, silver and/or gold,
a" is from 0.1 to 1,
b" is from 0.2 to 2,
c" is from 3 to 10,
d" is from 0.02 to 2,
e" is from 0.01 to 5, preferably from 0.1 to 3,
f" is from 0 to 5,
g" is from 0 to 10,
h" is from 0 to 1,
x",y" are numbers which are determined by the valency and frequency of the elements other than oxygen in III, and
p",q" are numbers whose ratio p"/q" is from 0.1 to 5, preferably from 0.5 to 2, very particular preferred materials III being those in which $Z^2_{b''}$ is (tungsten)$_{b''}$ and $Z^2_{12}$ is (molybdenum)$_{12}$.

It is also advantageous if at least 25 mol % (preferably at least 50, particularly preferably at least 100, mol %) of the total amount $[Y^1{}_aY^2{}_{b'}O_{x'}]_p([Bi_{a''}Z^2{}_{b''}O_{x''}]_{p''})$ of the multimetal oxide materials II suitable according to the invention as fixed-bed catalysts 1 (multimetal oxide materials III) are present in the multimetal oxide materials II suitable according to the invention (multimetal oxide materials III) in the form of three-dimensional regions which are delimited from their local environment as a result of their chemical composition differing from their local environment and have the chemical composition $Y^1{}_aY^2{}_{b'}O_{x'}[Bi_{a''}Z^2{}_{b''}O_{x''}]$ and whose maximum diameter is from 1 nm to 100 μm.

Regarding the shaping of the catalyst comprising multimetal oxide materials II, the statements made in connection with the catalysts comprising multimetal oxide materials I are applicable.

The preparation of active material comprising multimetal oxide materials II is described, for example, in EP-A 575897 and in DE-A 19855913.

It is expedient in terms of application technology to carry out the first reaction stage of the novel process in a two-zone tube-bundle reactor. A preferred variant of a two-zone tube-bundle reactor which can be used according to the invention is disclosed in DE-C 2830765. However, the two-zone tube-bundle reactors disclosed in DE-C 2513405, U.S. Pat. No. 3,147,084, DE-A 2201528, EP-A 383224 and DE-A 2903218 are also suitable for carrying out the first stage of the novel process.

In other words, in the simplest procedure, the fixed-bed catalyst 1 to be used according to the invention is present in the metal tubes of the tube-bundle reactor, and two thermostating media, as a rule salt melts, essentially spatially separated from one another are passed around the metal tubes. The tube section over which the respective salt bath extends represents, according to the invention, a reaction zone, i.e. in the simplest procedure a salt bath A flows around that section of the tubes (the reaction zone A) in which the oxidative conversion of the propene (in a single pass) up to a conversion of from 40 to 80 mol % takes place, and a salt bath B flows around that section of the tube (reaction zone B), in which the subsequent oxidative conversion of the propene (in a single pass) to a conversion of at least 90 mol % takes place (if necessary, the reaction zones A,B to be used according to the invention may be followed by further reaction zones which are kept at individual temperatures).

It is expedient in terms of application technology if the first reaction stage of the novel process comprises no further reaction zones, i.e. the salt bath B expediently flows around those sections of the tubes in which the subsequent oxidative conversion of the propene (in a single pass) to a conversion of ≧92 mol % or ≧94 mol % or more takes place.

Usually, the beginning of reaction zone B is behind the maximum hot spot of reaction zone A. The maximum hot spot of reaction zone B is usually below the maximum hot spot temperature of reaction zone A.

According to the invention, the two salt baths A,B can be fed cocurrent or countercurrent through the space surrounding the reaction tubes, relative to the direction of flow of the reaction gas mixture flowing through the reaction tubes. According to the invention, it is of course also possible to use cocurrent flow in the reaction zone A and countercurrent flow in the reaction zone B (or vice versa).

In all abovementioned configurations, a transverse flow can be superposed, within the respective reaction zone, on the salt melt flow parallel to the reaction tubes, so that the individual reaction zone corresponds to a tube-bundle reactor described in EP-A 700714 or in EP-A 700893, and in general a meandering flow of the heat-exchange medium results in the longitudinal section through the catalyst tube bundle.

Expediently, the reaction gas starting mixture 1 is preheated to the reaction temperature before being fed to the catalyst load 1.

In the abovementioned tube-bundle reactors, the catalyst tubes are usually made of ferritic steel and typically have a wall thickness of from 1 to 3 mm. Their internal diameter is as a rule from 20 to 30 mm, frequently from 22 to 26 mm. It is expedient in terms of application technology if the number of catalyst tubes housed in the tube-bundle container is at least 5000, preferably at least 10,000. Frequently, the number of catalyst tubes housed in the reaction container is from 15,000 to 30,000. Tube-bundle reactors having more than 40,000 catalyst tubes tend to be the exception. Within the container, the catalyst tubes are usually homogeneously distributed, the distribution expediently being chosen so that the distance between the central inner axes of catalyst tubes closest to one another (i.e. the catalyst tube spacing) is from 35 to 45 mm (cf. for example EP-B 468290).

Particularly suitable heat exchange media are fluid thermostating media. The use of melts of salts such as potassium nitrate, potassium nitrite, sodium nitrite and/or sodium nitrate, or of metals having a low melting point, such as sodium, mercury and alloys of various metals, is particularly advantageous.

In all abovementioned configurations of the flow in the two-zone tube-bundle reactors, the flow rate within the two required circulations of heat exchange medium is as a rule chosen so that the temperature of the heat exchange medium increases by from 0 to 15° C. from the entrance into the reaction zone to the exit out of the reaction zone, i.e., according to the invention, the abovementioned ΔT may be from 1 to 10° C., or from 2 to 8° C. or from 3 to 6° C.

The temperature of the heat exchange medium on entering the reaction zone A is, according to the invention, usually from 300 to 390° C. or to 350° C. The temperature of the heat exchange medium on entering the reaction zone B is, according to the invention, usually, on the one hand, from 305 to 420° C. or to 380° C. and, on the other hand, simultaneously at least 5° C. above the temperature of the heat exchange medium on entering the reaction zone A. Preferably, the temperature of the heat exchange medium on entering the reaction zone B is at least 10° C. above the temperature of the heat exchange medium on entering the reaction zone A. The difference between the temperatures on entry into the reaction zones A and B can, according to the invention, thus be up to 20° C., up to 25° C., up to 30° C., up to 40° C., up to 45° C. or up to 50° C. Usually, however, the abovementioned temperature difference is not more than 50° C. The higher the chosen propene loading of the catalyst bed 1 in the novel process, the greater should be the difference between the temperature of the heat exchange medium on entering the reaction zone A and the temperature of the heat exchange medium on entering the reaction zone B.

According to the invention, the temperature of the heat exchange medium on entering the reaction zone B is advantageously from 305 to 365° C. or 340° C., particularly advantageously from 310 to 330° C.

In the novel process, the two reaction zones A, B can of course also be realized in tube-bundle reactors spatially separated from one another. If required, a heat exchanger may also be installed between the two reaction zones A, B. The two reaction zones A, B can of course also be in the form of a fluidized bed.

In the novel process, it is also possible to use catalyst beds 1 whose volume-specific activity in the direction of flow of the reaction gas starting mixture 1 increases continuously, abruptly or stepwise (this can be effected as described in WO 98/24746 or in JP-A 91/294239 or by dilution with inert material). Furthermore, the inert diluent gases (e.g. only propane or only methane etc.) recommended in EP-A 293224 and in EP-B 257565 may also be used for the two-zone procedure described. The latter may, if required, also be combined with a volume-specific activity of the catalyst bed which increases in the direction of flow of the reaction gas mixture.

It should also be pointed out once again here that, for carrying out the reaction stage 1 of the novel process, in particular the two-zone tube-bundle reactor type described in German Published Application DE-B 2,201,528 may be used, said reactor type providing the possibility of transferring some of the hotter heat exchange medium of reaction zone B to reaction zone A in order, if required, to heat up a cold reaction gas starting mixture or a cold recycle gas. Furthermore, the tube bundle characteristics within the individual reaction zone can be designed as described in EP-A 382098.

According to the invention, it has proven expedient to cool the product gas mixture leaving the first reaction stage before entry into the second reaction stage, in order thus to suppress subsequent complete combustion of parts of the acrolein formed in the first reaction stage. For this purpose, an after-cooler is usually connected between the two reaction stages. In the simplest case, this may be an indirect tube-bundle heat exchanger. The product gas mixture is as a rule passed through the tubes, and a heat exchange medium, the type of which may correspond to the heat exchange media recommended for the tube-bundle reactors, is passed around the tubes. The interior of the tubes is advantageously filled with inert packings (e.g. stainless steel spirals, steatite rings, steatite beads, etc.). These improve the heat exchange and trap any molybdenum trioxide subliming from the fixed catalyst bed of the first reaction stage before it enters the second reaction stage. It is advantageous if the aftercooler is made of stainless steel coated with zinc silicate paint.

In terms of application technology, the product gas mixture of the first reaction stage is expediently cooled in the aftercooler described above to a temperature of from 210 to 290° C., frequently from 220 to 260° C. or from 225 to 245° C., i.e. the cooling of the product gas mixture of the first reaction stage can certainly be effected to temperatures which are below the temperature of the reaction zone C. However, the aftercooling described is by no means essential and can as a rule be omitted, especially when the path of the product gas mixture from the first reaction stage to the second reaction stage is kept short. Usually, the novel process is furthermore realized in a manner such that the oxygen demand in the second reaction stage is not covered by a correspondingly high oxygen content of the reaction gas starting mixture 1, but the required oxygen is added in the region between first and second reaction stages. This can be effected before, during, after and/or for the aftercooling. A suitable source of the molecular oxygen required in the second reaction stage is either pure oxygen or a mixture of oxygen and inert gas, e.g. air or air depleted in molecular nitrogen (e.g. $\geq$90% by volume of $O_2$, $\leq$10% by volume of $N_2$). The oxygen source is usually added in the form compressed to the reaction pressure.

According to the invention, the acrolein fraction of the reaction gas starting mixture 2 thus produced may be, for example, from 3 to 15, frequently from 4 to 10, % by volume or from 5 to 8% by volume (based in each case on the total volume).

According to the invention, the molar ratio of $O_2$ to acrolein in the reaction gas starting mixture 2 must be $\geq$0.5. This ratio is frequently $\geq$1. Usually, this ratio is $\leq$3. According to the invention, the molar ratio of $O_2$ to acrolein in the reaction gas starting mixture 2 is frequently from 1 to 2 or from 1 to 1.5.

Frequently, the novel process is carried out with an acrolein:oxygen:steam:inert gas volume ratio (l(S.T.P.)) in the reaction gas starting mixture 2 of 1:(0.5 or 1 to 3):(0 to 20):(3 to 30), preferably of 1:(1 to 3):(0.5 to 10):(7 to 10).

The operating pressure in the second reaction stage may be either below atmospheric pressure (e.g. to 0.5 bar) or above atmospheric pressure. According to the invention, the operating pressure in the second reaction stage is typically from 1 to 5, frequently from 1 to 3, bar. Usually, the reaction pressure in the second reaction stage will not exceed 100 bar.

The reaction zone C preferably extends to an acrolein conversion of from 65 to 80 mol %. Moreover, the temperature of the reaction zone C is advantageously from 245 to 260° C. The temperature of the reaction zone D is preferably at least 20° C. above the temperature of the reaction zone C and is advantageously from 265 to 285° C.

The higher the acrolein loading of the catalyst bed 2 in the novel process, the greater should be the chosen difference between the temperature of the reaction zone C and the temperature of the reaction zone D. Usually, however, the abovementioned temperature difference in the novel process is not more than 40° C., i.e. the difference between the temperature of the reaction zone C and the temperature of the reaction zone D may be, according to the invention, up to 10° C., up to 15° C., up to 25° C., up to 30° C., up to 35° C. or up to 40° C.

Otherwise, the acrolein conversion, based on a single pass through the second reaction stage, in the novel process may be $\geq$92 mol % or $\geq$94 mol % or $\geq$96 mol % or $\geq$98 mol % and frequently even $\geq$99 mol %. The selectivity of the acrolein formation, based on acrolein converted, is usually $\geq$92 mol % or $\geq$94 mol %, frequently $\geq$95 mol % or $\geq$96 mol % or $\geq$97 mol %.

Surprisingly, the abovementioned applies not only in the case of acrolein loadings of the catalyst bed 2 of $\geq$140 l(S.T.P.)/l·h or $\geq$150 l(S.T.P.)/l·h or of $\geq$160 l(S.T.P.)/l·h or $\geq$170 l(S.T.P.)/l·h or $\geq$175 l(S.T.P.)/l·h or $\geq$180 l(S.T.P.)/l·h, but also in the case of acrolein loadings of the catalyst bed of $\geq$185 l(S.T.P.)/l·h or of $\geq$190 l(S.T.P.)/l·h or $\geq$200 l(S.T.P.)/l·h or $\geq$210 l(S.T.P.)/l·h and in the case of loadings $\geq$220 l(S.T.P.)/l·h or $\geq$230 l(S.T.P.)/l·h or 240 l(S.T.P.)/l·h or $\geq$250 l(S.T.P.)/l·h.

It is surprising that the abovementioned values are achievable even if the inert gas used according to the invention in the second reaction stage comprises ≧30% by volume or ≧40% by volume or ≧50% by volume or ≧60% by volume or ≧70% by volume or ≧80% by volume or ≧90% by volume or ≧95% by volume of molecular nitrogen.

Expediently, the inert diluent gas in the second reaction stage in the novel process comprises from 5 to 20% by weight of H$_2$O (formed in the first reaction stage) and from 70 to 90% by volume of N$_2$.

Apart from the components stated in this document, the reaction gas starting mixture 2 usually contains essentially no further components.

In the case of acrolein loadings of the second fixed-bed catalyst above 250 l(S.T.P.)/l·h, the presence of inert diluent gases such as propane, ethane, methane, butane, pentane, CO$_2$, CO, steam and/or noble gases, is recommended for the reaction gas starting mixture 2. However, these gases may of course also be present even at lower acrolein loadings. It is surprising that the novel process can be carried out using a catalyst bed which is homogeneous, i.e. chemically uniform, over both reaction zones C, D, without suffering significant declines in conversion and/or selectivity.

In the novel process, the acrolein loading of the second fixed-bed catalyst will as a rule not exceed 600 l(S.T.P.)/l·h. Typically, the acrolein loadings of the catalyst bed 2 of the novel process, without significant decline in conversion and selectivity, are ≦300 l(S.T.P.)/l·h, frequently ≦250 l(S.T.P.)/l·h.

In the novel process, the acrolein loading of the second catalyst bed is as a rule about 10, frequently about 20 or 25, l(S.T.P.)/l·h below the propene loading of the first catalyst bed. This is primarily due to the fact that, in the first reaction stage, both conversion and selectivity do not as a rule reach 100%. Furthermore, the oxygen demand of the second reaction stage is usually covered by air.

It is to be noted that, in the novel process, the selectivity, balanced over both reaction stages, of the acrylic acid formation is as a rule ≧83 mol %, frequently ≧85 mol % or ≧88 mol %, often ≧90 mol % or ≧93 mol %, based on propene converted, even at the highest propene and acrolein loadings.

Suitable fixed-bed catalysts 2 for the gas-phase catalytic acrolein oxidation in the second reaction stage are all those whose active material is at least one Mo and V containing multimetal oxide.

Multimetal oxide catalysts suitable in this manner are described, for example, in U.S. Pat. Nos. 3,775,474, 3,954,855, 3,893,951 and 4,339,355. The multimetal oxide materials of EP-A 427 508, of DE-A 2 909 671, of DE-C 31 51 805, of German Published Application DE-B 2,626,887, of DE-A 43 02 991, of EP-A 700 893, of EP-A 714 700 and of DE-A 19 73 6105 are furthermore particularly suitable. Particularly preferred in this context are the exemplary embodiments of EP-A 714 700 and of DE-A 19 73 6105.

A large number of the multimetal oxide active materials suitable as fixed-bed catalysts 2 can be subsumed under the formula IV

 (IV), where
X$^1$ is W, Nb, Ta, Cr and/or Ce,
X$^2$ is Cu, Ni, Co, Fe, Mn and/or Zn,
X$^3$ is Sb and/or Bi,
X$^4$ is one or more alkali metals,
X$^5$ is one or more alkaline earth metals,
X$^6$ is Si, Al, Ti and/or Zr,
a is from 1 to 6,
b is from 0.2 to 4,
c is from 0.5 to 18,
d is from 0 to 40,
e is from 0 to 2,
f is from 0 to 4,
g is from 0 to 40 and
n is a number which is determined by the valency and frequency of the elements other than oxygen in IV.

Preferred embodiments within the active multimetal oxides IV are those which have the following meanings of the variables of the formula IV:
X$^1$ is W, Nb and/or Cr,
X$^2$ is Cu, Ni, Co and/or Fe,
X$^3$ is Sb,
X$^4$ is Na and/or K,
X$^5$ is Ca, Sr and/or Ba,
x$^6$ is Si, Al and/or Ti,
a is from 1.5 to 5,
b is from 0.5 to 2,
c is from 0.5 to 3,
d is from 0 to 2,
e is from 0 to 0.2,
f is from 0 to 1 and
n is a number which is determined by the valency and frequency of the elements other than oxygen in IV.

Very particulary preferred multimetal oxides IV are, however, those of the formula V

 (V)

where
Y$^1$ is W and/or Nb,
y$^2$ is Cu and/or Ni,
y$^5$ is Ca and/or Sr,
y$^6$ is Si and/or Al,
a' is from 2 to 4,
b' is from 1 to 1.5,
c' is from 1 to 3,
f' is from 0 to 0.5,
g' is from 0 to 8 and
n' is a number which is determined by the valency and frequency of the elements other than oxygen in V.

The multimetal oxide active materials (IV) suitable according to the invention are obtainable in a manner which is known per se and is, for example, disclosed in DE-A 4335973 or in EP-A 714700.

In principle, multimetal oxide active materials suitable according to the invention as fixed-bed catalysts 2, in articular those of the formula IV, can be prepared in a simple manner by producing, from suitable sources of their elemental constituents, a very intimate, finely divided dry blend having a composition corresponding to their stoichiometry, and calcining said dry blend at from 350 to 600° C. The calcination can be carried out either under inert gas or under an oxidizing atmosphere, e.g. air (mixture of inert gas and oxygen) or under reducing atmosphere (e.g. mixtures of inert gas and reducing gases such as H$_2$, NH$_3$, CO, methane and/or acrolein or said reducing gases by themselves). The duration of calcination may be from a few minutes to a few hours and usually decreases with increasing temperature. Suitable sources of the elemental constituents of the multimetal oxide active materials IV are those compounds which are oxides and/or those compounds which can be converted into oxides by heating, at least in the presence of oxygen.

The thorough mixing of the starting compounds for the preparation of multimetal oxide materials IV can be effected in dry or in wet form. If it is carried out in dry form, the starting compounds are expediently used in the form of finely divided powders and, after mixing and, if required, compaction, are subjected to calcination. However, the thorough mixing is preferably effected in wet form.

Usually, the starting compounds are mixed with one another in the form of an aqueous solution and/or suspension. Particularly intimate dry blends are obtained in the mixing process described when exclusively dissolved sources of the elemental constituents are used as starting materials. A preferably used solvent is water. The aqueous material obtained is then dried, the drying process preferably being carried out by spray-drying the aqueous mixture at outlet temperatures of from 100 to 150° C.

The multimetal oxide materials suitable according to the invention as fixed-bed catalysts 2, in particular those of the formula IV, can be used for the novel process both in powder form and after shaping into specific catalyst geometries, it being possible to carry out the shaping before or after the final calcination. For example, unsupported catalysts can be prepared from the powder form of the active material or its uncalcined precursor material by compaction to give the desired catalyst geometry (for example by pelleting or extrusion), if necessary assistants, e.g. graphite or stearic acid as lubricants and/or molding assistants and reinforcing agents, such as microfibers of glass, asbestos, silicon carbide or potassium titanate, being added. Suitable unsupported catalyst geometries are, for example, solid cylinders or hollow cylinders having an external diameter and a length of from 2 to 10 mm. In the case of the hollow cylinders, a wall thickness of from 1 to 3 mm is expedient. Of course, the unsupported catalyst may also have spherical geometry, it being possible for the sphere diameter to be from 2 to 10 mm.

Of course, the shaping of the pulverulent active material or its pulverulent, still uncalcined precursor material can also be effected by application to preshaped inert catalyst supports. The coating of the supports for the preparation of the coated catalyst is carried out as a rule in a suitable rotatable container, as disclosed, for example, in DE-A 2909671, EP-A 293859 or EP-A 714700.

For coating the support, the powder material to be applied is expediently moistened and, after the application, is dried again, for example by means of hot air. The coat thickness of the powder material applied to the support is expediently chosen to be from 10 to 1000 µm, preferably from 50 to 500 µm, particularly preferably from 150 to 250 µm.

The support materials used may be conventional porous or nonporous aluminas, silica, thorium dioxide, zirconium dioxide, silicon carbide or silicates, such as magnesium silicate or aluminum silicate. The supports may have a regular or irregular shape, those having a regular shape with pronounced surface roughness, for example spheres or hollow cylinders, being preferred. The use of essentially nonporous, spherical steatite supports which have a rough surface and whose diameter is from 1 to 8 mm, preferably from 4 to 5 mm, is suitable. However, the use of cylinders whose length is from 2 to 10 mm and whose external diameter is from 4 to 10 mm as supports is also suitable. When rings suitable according to the invention are used as supports, the wall thickness is moreover usually from 1 to 4 mm. Annular supports preferably to be used according to the invention have a length of from 3 to 6 mm, an external diameter of from 4 to 8 mm and a wall thickness of from 1 to 2 mm. Rings of 7 mm×3 mm×4 mm (external diameter×length×internal diameter) are also particularly suitable according to the invention as supports. The fineness of the catalytically active oxide materials to be applied to the surface of the support is of course adapted to the desired coat thickness (cf. EP-A 714 700).

Advantageous multimetal oxide active materials to be used according to the invention as fixed-bed catalysts 2 are furthermore materials of the formula VI $$[D]_p[E]_q \quad (VI),$$

where
D is $Mo_{12}V_{a''}Z^1_{b''}Z^2_{c''}Z^3_{d''}Z^4_{e''}Z^5_{f''}Z^6_{g''}O_{x''}$,
E is $Z^7_{12}Cu_{h''}H_{i''}O_{y''}$,
$Z^1$ is W, Nb, Ta, Cr and/or Ce,
$Z^2$ is Cu, Ni, Co, Fe, Mn and/or Zn,
$Z^3$ is Sb and/or Bi,
$Z^4$ is Li, Na, K, Rb, Cs and/or H
$Z^5$ is Mg, Ca, Sr and/or Ba,
$Z^6$ is Si, Al, Ti and/or Zr,
$Z^7$ is Mo, W, V, Nb and/or Ta,
a" is from 1 to 8,
b" is from 0.2 to 5,
c" is from 0 to 23,
d" is from 0 to 50,
e" is from 0 to 2,
f" is from 0 to 5,
g" is from 0 to 50,
h" is from 4 to 30,
i" is from 0 to 20 and
X", y" are numbers which are determined by the valency and frequency of the elements other than oxygen in VI and
p,q are numbers other than zero whose ratio p/q is from 160:1 to 1:1, which are available by separately preforming a multimetal oxide material E $$Z^7_{12}Cu_{h''}H_{i''}O_{y''} \quad (E),$$

in finely divided form (starting material 1) and then incorporating the preformed solid starting material 1 into an aqueous solution, aqueous suspension or a finely divided dry blend of sources of the elements Mo, V, $Z^1$, $Z^2$, $Z^3$, $Z^4$, $Z^5$, $Z^6$, which contains the abovementioned elements in the stoichiometry D $$Mo_{12}V_{a''}Z^1_{b''}Z^2_{c''}Z^3_{d''}Z^4_{e''}Z^5_{f''}Z^6_{g''} \quad (D)$$

(starting material 2), in the desired ratio p:q, drying any resulting aqueous mixture, and calcining the resulting precursor material at from 250 to 600° C., before or after it has been dried, to give the desired catalyst geometry.

The multimetal oxide materials VI in which the preformed solid starting material 1 is incorporated into an aqueous starting material 2 at ≦70° C. are preferred. A detailed description of the preparation of catalysts comprising multimetal oxide materials VI is contained, for example, in EP-A 668104, DE-A 19736105 and DE-A 19528646.

Regarding the shaping, the statements made in connection with the catalysts comprising multimetal oxide material IV are applicable to catalysts comprising multimetal oxide materials VI.

In terms of application technology, the second reaction stage of the novel process is expediently carried out in a two-zone tube-bundle reactor. A preferred variant of a two-zone tube-bundle reactor which can be used according to the invention for the second reaction stage is disclosed in DE-C 2830765. However, the two-zone tube-bundle reactors disclosed in DE-C 2513405, U.S. Pat. No. 3,147,084, DE-A 2201528, EP-A 383224 and DE-A 2903582 are also suitable for carrying out the second reaction stage of the novel process.

In other words, in a simple procedure, the fixed-bed catalyst to be used according to the invention is present in the metal tubes of a tube-bundle reactor, and two thermostating media, as a rule salt melts, which are essentially spatially separated from one another are passed around the metal tubes. The tube section over which the respective salt bath extends represents, according to the invention, a reaction zone.

In other words, in a simple procedure, a salt bath C flows around those sections of the tubbes (the reaction zone C) in which the oxidative conversion of the acrolein (in a single pass) to a conversion of from 55 to 85 mol % takes place, and a salt bath D flows around the section of the tubes (the reaction zone D) in which the subsequent oxidative conversion of the acrolein (in a single pass) takes place to a conversion of at least 90 mol % (if required, the reaction zones C, D to be used according to the invention may be followed by further reaction zones which are kept at individual temperatures).

In terms of application technology, the reaction stage 2 of the novel process expediently comprises no further reaction zones, i.e. salt bath D expediently flows around that section of the tubes in which the subsequent oxidative conversion of the acrolein (in a single pass) takes place to a conversion of ≧92 mol % or ≧94 mol % or ≧96 mol % or ≧98 mol % and frequently even ≧99 mol % or more.

Usually, the beginning of the reaction zone D is behind the maximum hot spot of the reaction zone C. The temperature of the maximum hot spot of the reaction zone D is usually below the maximum hot spot temperature of the reaction zone C.

According to the invention, the two salt baths C, D can be passed cocurrent or countercurrent through the space surrounding the reaction tubes, relative to the direction of flow of the reaction gas mixture flowing through the reaction tubes. According to the invention, it is of course also possible to use cocurrent flow in reaction zone C and countercurrent flow in reaction zone D (or vice versa).

In all abovementioned configurations within the respective reaction zone, a transverse flow can be superposed on the flow of the salt melt parallel to the reaction tubes, so that the individual reaction zone corresponds to a tube-bundle reactor as described in EP-A 700714 or in EP-A 700893 and overall a meandering flow of the heat exchange medium results in the longitudinal section through the catalyst tube bundle.

In the abovementioned tube-bundle reactors, the catalyst tubes are usually made of ferritic steel and typically have a wall thickness of from 1 to 3 mm. Their internal diameter is as a rule from 20 to 30 mm, frequently from 22 to 26 mm. It is expedient in terms of application technology if the number of catalyst tubes housed in the tube-bundle container is at least 5000, preferably at least 10,000. Frequently, the number of catalyst tubes housed in the reaction container is from 15,000 to 30,000. Tube-bundle reactors having more than 40,000 catalyst tubes tend to be the exception. Within the container, the catalyst tubes are usually homogeneously distributed, the distribution expediently being chosen so that the distance between the central inner axes of catalyst tubes closest together (the catalyst tube spacing) is from 35 to 45 mm (cf. EP-B 468290).

Suitable heat exchange media are in particular fluid thermostating media. The use of melts of salts, such as potassium nitrate, potassium nitrite, sodium nitrite and/or sodium nitrate, or of metals having a low melting point, such as sodium, mercury and alloys of various metals, is particularly advantageous.

As a rule, in all abovementioned configurations of the flow in the two-zone tube-bundle reactors, the flow rate within the two required circulations of heat exchange media is chosen so that the temperature of the heat exchange medium increases by from 0 to 15° C. from the entrance into the reaction zone to the exit from the reaction zone, i.e. the abovementioned ΔT can, according to the invention, be from 1 to 10° C. or from 2 to 8° C. or from 3 to 6° C.

According to the invention, the temperature of the heat exchange medium on entering the reaction zone C is usually from 230 to 270° C. According to the invention, the temperature of the heat exchange medium on entering the reaction zone D is usually on the one hand from 250 to 300° C. and, on the other hand, is simultaneously at least 5° C. and frequently at least 10° C. above the temperature of the heat exchange medium on entry into the reaction zone C.

Preferably, the temperature of the heat exchange medium on entering the reaction zone D is at least 20° above the temperature of the heat exchange medium on entering the reaction zone C. The difference between the temperatures of entry into the reaction zones C and D may thus be, according to the invention, up to 15° C., up to 25° C., up to 30° C., up to 35° C. or up to 40° C. Usually, however, the abovementioned temperature is not more than 50° C. The higher the acrolein loading of the catalyst bed 2 in the novel process, the greater should the difference between the temperature of the heat exchange medium on entering the reaction zone C and the temperature of the heat exchange medium on entering the reaction zone D be. Preferably, the temperature on entering the reaction zone D is from 245 to 260° C. and the temperature on entering the reaction zone D is from 265 to 285° C.

In the novel process, the two reaction zones C, D can of course also be realized in tube-bundle reactors spatially separated from one another. If required, a heat exchanger may also be mounted between the two reaction zones C, D. The two reaction zones C, D can of course also be designed as a fluidized bed.

Furthermore, in the novel process, it is also possible to use catalyst beds 2 whose volume-specific activity increases continuously, abruptly or stepwise in the direction of flow of the reaction gas mixture (this can be achieved, for example, by dilution with inert material or variation of the activity of the multimetal oxide).

Moreover, the inert diluent gases (e.g. only propane or only methane, etc) recommended in EP-A 293224 and in EP-B 257565 may also be used for the two-zone procedure described, in the second reaction stage. The latter may if required also be combined with a volume-specific activity of the catalyst bed 2 which decreases in the direction of flow of the reaction gas mixture.

It should once again be pointed out here that in particular the two-zone tube-bundle reactor type described in German Published Application DE-B 2,201,528 can also be used for a procedure in the second reaction stage of the novel process, said reactor type providing the possibility of transferring a part of the hotter heat exchange medium from the reaction zone D to the reaction zone C in order, if required, to heat up a reaction gas starting mixture 2 which is too cold or a cold recycle gas. Furthermore, the tube-bundle characteristics within an individual reaction zone can be designed as described in EP-A 382 098.

The novel process is particularly suitable for a continuous procedure. It is surprising that it permits, in a single pass, a high space-time yield in the formation of a desired product without simultaneously significantly impairing the selectivity of the formation of the desired product. Rather, a high selectivity in the formation of a desired product generally tends to be observed. The latter is presumably due to the fact that, owing to the higher temperatures present in the region of higher propene or acrolein conversion, the novel process gives rise to less readsorption of resulting acrolein/acrylic acid onto the fixed-bed catalyst.

Also remarkable is the fact that the catalyst life in the novel process is completely satisfactory in spite of the extreme catalyst loading with reactants.

The novel process gives not pure acrylic acid but a mixture from whose secondary components the acrylic acid can be separated in a manner known per se (for example by rectification and/or crystallization). Unconverted acrolein, propene and inert diluent gas used and/or formed in the course of the reaction can be recycled to the gas-phase oxidation. In the novel two-stage gas-phase oxidation starting from propene, the recycling is expediently effected to the first oxidation stage. Of course, the novel procedure can if required also be used in the case of conventional propene loads.

Otherwise, unless stated otherwise, conversion, selectivity and residence time are defined as follows in this document:

$$\text{Conversion of starting material (\%)} = \frac{\text{number of moles of starting material converted}}{\text{number of moles of starting materials used}} \times 100$$

$$\text{Selectivity of product formation} = \frac{\text{number of moles of starting material converted to product}}{\text{number of moles of starting material converted}} \times 100$$

$$\text{Residence time (sec)} = \frac{\text{empty reactor volume filled with catalyst (l)}}{\text{throughput of reaction gas starting mixture (l (S.T.P.))}} \times 3600$$

EXAMPLES AND COMPARATIVE EXAMPLES a) Preparation of the Fixed-bed Catalyst 1

1. Preparation of a Starting Material 1

209.3 kg of tungstic acid (72.94% by weight of W) were stirred in portions into 775 kg of an aqueous solution of bismuth nitrate in nitric acid (11.2% by weight of Bi, from 3 to 5% by weight of free nitric acid; density: from 1.22 to 1.27 g/ml) at 25° C. The resulting aqueous mixture was then stirred for a further 2 hours at 25° C. and then spray-dried.

The spray-drying was carried out in a rotary-disk spray tower by the countercurrent procedure at a gas inlet temperature of 300±10° C. and a gas outlet temperature of 100±10° C. The spray-dried powder obtained was then calcined at from 780 to 810° C. (in a rotary tubular furnace through which air flowed (1.54 m³ internal volume, 200 m³ (S.T.P.) of air/h)). It is important that the calcination temperature is accurately set in accordance with the desired phase composition of the calcination product. The phases $WO_3$ (monoclinic) and $Bi_2W_2O_9$ are desired; the presence of γ-$Bi_2WO_6$ (russellite) is undesired. If therefore, after the calcination, the compound γ-$Bi_2WO_6$ is still detectable on the basis of a reflection at a reflection angle of 2-=28.4° (CuKα radiation) in the powder X-ray diffraction pattern, the preparation should be repeated and the calcination temperature should be increased within the stated temperature range until the reflection disappears. The preformed calcined mixed oxide thus obtained was milled so that the $X_{50}$ value (cf. Ullmann's Encyclopedia of Industrial Chemistry, 6$^{th}$ Edition (1998) Electronic Release, Section 3.1.4 or DIN 66141) of the resulting particles was 5 μm. The milled material was then mixed with 1% by weight (based on the milled material) of finely divided $SiO_2$ (bulk density 150 g/l; $X_{50}$ value of the $SiO_2$ particles was 10 μm, the BET surface area was 100 m²/g).

2. Preparation of a Starting Material 2

A solution A was prepared by dissolving 213 kg of ammonium heptamolybdate in 600 l of water at 60° C. while stirring, and adding 0.97 kg of an aqueous potassium hydroxide solution (46.8% by weight of KOH) at 20° C. to the resulting solution while maintaining the 60° C. and stirring.

A solution B was prepared by introducing 116.25 kg of an aqueous iron nitrate solution (14.2% by weight of Fe) in 262.9 kg of an aqueous cobalt nitrate solution (12.4% by weight of Co) at 60° C. The solution B was then pumped continuously into the initially taken solution A over a period of 30 minutes while maintaining the 60° C. Stirring was then carried out for 15 minutes at 60° C. 19.16 kg of a silica gel (46.80% by weight of $SiO_2$, density: from 1.36 to 1.42 g/ml, pH from 8.5 to 9.5, alkali metal content not more than 0.5% by weight) were then added to the resulting aqueous mixture, after which stirring was carried out for a further 15 minutes at 60° C.

Spray-drying was then carried out in a rotary-disk spray tower by the countercurrent procedure (gas inlet temperature: 400±10° C., gas outlet temperature: 140±5° C.). The resulting spray-dried powder has a loss on ignition of about 30% by weight (ignition for 3 hours at 600° C.).

3. Preparation of the Multimetal Oxide Active Material

The starting material 1 was homogeneously mixed with the starting material 2 in the amount required for a multimetal oxide active material having the stoichiometry

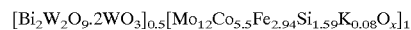

$[Bi_2W_2O_9.2WO_3]_{0.5}[Mo_{12}Co_{5.5}Fe_{2.94}Si_{1.59}K_{0.08}O_x]_1$

In addition, 1.5% by weight, based on the abovementioned total material, of finely divided graphite (sieve analysis: min. 50% by weight <24 μm, max. 10% by weight >24 μm and <48 μm, max. 5% by weight >48 μm, BET surface area: from 6 to 13 m²/g) were homogeneously mixed in. The resulting dry blend was compressed to give hollow cylinders having a length of 3 mm, an external diameter of 5 mm and a wall thickness of 1.5 mm and then subjected to a heat treatment as follows.

In a muffle furnace through which air flowed (60 l internal volume, 1 l/h of air per gram of precursor of the active material), heating was effected at a heating rate of 180° C./h, initially from room temperature (25° C.) to 190° C. This temperature was maintained for 1 hour and then increased to 210° C. at a heating rate of 60° C./h. The 210° C. was once again maintained for 1 hour before being increased at a heating rate of 60° C./h to 230° C. This temperature were likewise maintained for 1 hour before being increased to 265° C., once again at a heating rate of 60° C./h. The 265° C. were then likewise maintained for 1 hour. Thereafter, cooling was first effected at room temperature, and the decomposition phase was thus essentially complete. Heating was then effected at a heating rate of 180° C./h to 465° C., and this calcination temperature was maintained for 4 hours. A bed of the resulting unsupported catalyst rings formed the fixed-bed catalyst 1.

b) Preparation of the Fixed-bed Catalyst 2

1. Preparation of the Catalytically Active Oxide Material $Mo_{12}V_3W_{1.2}Cu_{2.4}O_n$ 190 g of copper(II) acetate monohydrate were dissolved in 2700 g of water to give a solution I. 860 g of ammonium heptamolybdate tetrahydrate, 143 g of ammonium metavanadate and 126 g of ammonium paratungstate heptahydrate were dissolved in succession in 5500 g of water at 95° C. to give a solution II. The solution I was then stirred all at once into the solution II, after which 25% strength by weight aqueous $NH_3$ solution was added in an amount such that a solution formed again. This was spray-dried at an outlet temperature of 110° C. The resulting spray-dried powder was kneaded with 0.25 kg, per kg of powder, of a 30% strength by weight aqueous acetic acid solution using a type ZS1-80 kneader from Werner & Pfleiderer and then dried at 110° C. for 10 hours in a drying oven.

700 g of the catalyst precursor thus obtained were calcined in an air/nitrogen mixture [(200 l of $N_2$/15 l of air)/h] in a rotary tubular furnace (50 cm long, 12 cm internal diameter). During the calcination, the kneaded material was continuously heated, initially from room temperature (about 25° C.) to 325° C. in the course of one hour. This temperature was then maintained for 4 hours. Heating was then effected to 400° C. in the course of 15 minutes, this temperature was maintained for 1 hour and the temperature was then brought to room temperature by cooling.

The calcined catalytically active material was milled to give a finely divided powder, 50% of the particles of said powder passing through a sieve of mesh size from 1 to 10 µm and said powder having a particle fraction of less than 1% with a maximum dimension above 50 µm.

2. Preparation of Coated Catalyst 28 kg of annular supports (7 mm external diameter, 3 mm length, 4 mm internal diameter, steatite, having a surface roughness Rz according to EP-B 714700 of 45 µm and having a total pore volume of ≦1% by volume, based on the volume of the supports, manufacturer: Caramtec DE) were introduced into a coating pan (angle of inclination 90°; Hicoater from Lödige, DE) having an internal volume of 200 l. The coating pan was then rotated at 16 rpm. 2000 g of an aqueous solution consisting of 75% by weight of $H_2O$ and 25% by weight of glycerol were then sprayed through a nozzle in the course of 25 minutes onto the supports. Simultaneously and in the same period, 0.7 kg of a catalytically active oxide powder from a) were metered in continuously via a vibrating channel, outside the spray cone of the atomizer nozzle. During the coating, the powder fed in was completely adsorbed onto the surface of the supports, an agglomeration of the finely divided oxidic active material was not observed. After the end of the addition of powder and aqueous solution, hot air at 110° C. was blown into the coating pan at a speed of 2 revolutions per minute for 20 minutes. The stationary bed was then dried for 2 hours at 250° C. under air (tray oven). Annular coated catalysts containing 20% by weight, based on the total material, of oxidic active material were obtained. The coat thickness was 230±25 µm, both over the surface of one support and over the surface of different supports. A bed of the resulting coated catalyst rings formed the fixed-bed catalyst 2.

c) Gas Phase Catalytic Oxidation of Propene to Acrylic Acid

1. The First Reaction Stage

A first reaction tube (V2A stainless steel; 30 mm external diameter; 2 mm wall thickness; 26 mm internal diameter, length: 439 cm, having a thermocouple tube (4 mm external diameter) centered in the middle of the reaction tube for holding a thermocouple with which the temperature in the reaction tube can be determined) was loaded from bottom to top, on a catalyst support ledge (44 cm long) first over a length of 30 cm with steatite beads having a rough surface (from 4 to 5 mm diameter; inert material for heating the reaction gas starting mixture 1) and then over a length of 300 cm with the unsupported catalyst rings prepared in a), before the loading was completed over a length of 30 cm with the abovementioned steatite beads as a subsequent bed. The remaining 35 cm of catalyst tube were left empty.

That part of the first reaction tube which had been loaded with solid was thermostated by means of 12 aluminum blocks which were cast in the form of a cylinder around the tube, were each 30 cm long and were heated by electric heating tapes (comparative experiments with a corresponding reaction tube heated by means of a salt bath through which nitrogen was bubbled showed that the thermostating by means of aluminum block was capable of simulating thermostating by means of a salt bath). The first six aluminum blocks in the direction of flow defined a reaction zone A and the remaining aluminum blocks defined a reaction zone B. Those ends of the reaction tube which were free of solid were kept at 220° C. by means of steam at superatmospheric pressure.

2. The Second Reaction Stage

A second reaction tube (V2A stainless steel; 30 mm external diameter; 2 mm wall thickness; 26 mm internal diameter, length: 439 cm, having a thermocouple tube (4 mm external diameter) centered in the middle of the reaction tube for holding a thermocouple with which the temperature in the reaction tube can be determined) was loaded from bottom to top on a catalyst support ledge (44 cm long) first over a length of 30 cm with steatite beads having a rough surface (from 4 to 5 mm diameter; inert material for heating the reaction gas starting mixture 2) and then over a length of 300 cm with the coated catalyst rings prepared in b), before the loading was completed over a length of 30 cm with the abovementioned steatite beads over a length of 30 cm as a subsequent bed. The remaining 35 cm of catalyst tube were left empty.

That part of the second reaction tube which had been loaded with solid was thermostated by means of 12 aluminum blocks which were cast in the form of a cylinder around the tube and each of which was 30 cm long (comparative experiments with a corresponding reaction tube heated by means of a salt bath through which nitrogen was bubbled showed that the thermostating by means of the aluminum blocks was capable of simulating thermostating by means of a salt bath). The first six aluminum blocks in the direction of flow defined a reaction zone C and the remaining six aluminum blocks defined a reaction zone D. Those ends of the reaction tube which were free of solid were kept at 220° C. by means of steam at superatmospheric pressure.

3. The Gas Phase Oxidation

The first reaction tube described above was fed with a reaction gas starting mixture having the following composition, the loading and the thermostating of the first reaction tube being varied:

from 6 to 6.5% by volume of propene,
from 3 to 3.5% by volume of $H_2O$, from 0.3 to 0.5% by volume of CO, from 0.8 to 1.2% by volume of $CO_2$, from 0.025 to 0.04% by volume of acrolein, from 10.4 to 10.7% by volume of $O_2$ and molecular oxygen as the remaining amount to 100%.

A small sample of the product gas mixture of the first reaction stage was taken at the exit of the first reaction tube, for gas a gas chromatographic analysis. Otherwise, the product gas mixture was fed directly into the subsequent stage for the oxidation of acrolein (to acrylic acid) while injecting air at a temperature of 25° C. (reaction stage 2). A small sample of the product gas mixture of the acrolein oxidation stage was likewise taken for a gas chromatographic analysis. Otherwise, the acrylic acid was separated from the product gas mixture of the second reaction stage in a manner known per se, and a part of the residual gas was reused for feeding the propene oxidation stage (as recycle gas), which explains the acrolein content of the abovementioned feed gas and the small variation of the feed composition.

The pressure at the entrance of the first reaction tube varied as a function of the chosen propene loading, in the range from 3.0 to 0.9 bar. An analysis point was also present at the end of the reaction zones A, C. The pressure at the entrance of the second reaction tube varied as a function of the acrolein loading, in the range from 2 to 0.5 bar.

The results achieved depending on the chosen loadings and the chosen aluminum thermostating and the air feed implemented (after the first reaction stage) are shown in the table below.

$T_A$, $T_B$, $T_C$, $T_D$ are the temperatures of the aluminum blocks in the reaction zones A, B, C and D.

$C_{PA}$ is the propene conversion at the end of the reaction zone A.

$C_{PB}$ is the propene conversion at the end of the reaction zone B.

$S_{DP}$ is the selectivity of the acrolein formation and of the acrylic acid byproduct formation together after the first reaction stage and based on propene converted.

$C_{AC}$ is the acrolein conversion at the end of the reaction zone C.

$C_{AD}$ is the acrolein conversion at the end of the reaction zone D.

$C_{PD}$ is the propene conversion at the end of the reaction zone D.

$S_{AA}$ is the selectivity of the acrylic acid formation after the second reaction stage and based on propene converted.

$STY_{AA}$ is the space-time yield of acrylic acid at the exit from the second reaction tube.

R is the molar ratio of molecular oxygen to acrolein in the reaction gas starting mixture 2.

M is the amount of air injected after the first reaction stage.

TABLE

| Propene loading [l(S.T.P.) of propene/l · h] | $T_A$ [° C.] | $T_B$ [° C.] | $C_{PA}$ (%) | $C_{PB}$ (%) | $S_{DP}$ (%) | M (l (S.T.P.)/ h) | R |
|---|---|---|---|---|---|---|---|
| 125 | 316 | 316 | 78.2 | 94.1 | 97.8 | 490 | 1.40 |
| 175 | 328 | 328 | 79.9 | 94.6 | 96.6 | 685 | 1.42 |
| 175 | 320 | 341 | 72.1 | 95.0 | 97.4 | 680 | 1.37 |
| 200 | 325 | 347 | 73.7 | 94.5 | 98.1 | 775 | 1.38 |

TABLE-continued

| Acrolein loading [l(S.T.P.) of acrolein/l · h] | $T_C$ [° C.] | $T_D$ [° C.] | $C_{AC}$ (%) | $C_{AD}$ (%) | $C_{PD}$ (%) | $S_{AA}$ (%) | $STY_{AA}$ (g/l · h) |
|---|---|---|---|---|---|---|---|
| 107 | 262 | 262 | 92.3 | 99.3 | 94.1 | 95.4 | 162.5 |
| 148 | 267 | 267 | 93.2 | 99.3 | 94.6 | 95.2 | 225.3 |
| 152 | 254 | 270 | 76.1 | 99.3 | 95.0 | 95.8 | 232.2 |
| 173 | 257 | 273 | 78.3 | 99.4 | 94.5 | 95.8 | 264.0 |

We claim:

1. A process for the catalytic gas-phase oxidation of propene to acrylic acid, comprising:

passing a reaction gas starting mixture 1 which comprises molecular oxygen and propene in a molar $O_2:C_3H_6$ ratio of $\geq 1$, and at least one inert gas which comprises at least 20% by volume of molecular nitrogen, in a first reaction stage at elevated temperatures, over a first fixed-bed catalyst, whose active material is at least one multimetal oxide comprising at least one of molybdenum and tungsten, and at least one of bismuth, tellurium, antimony, tin and copper thereby obtaining a product gas mixture 1;

wherein said passing of said reaction gas starting mixture 1 proceeds in such a way that a propene conversion in a single pass is $\geq 90$ mol %, an associated selectivity of an acrolein formation and of an acrylic acid byproduct formation together is $\geq 90$ mol %, optionally, a temperature of said product gas mixture 1 leaving said first reaction stage is reduced by indirect and/or direct cooling, and optionally, molecular oxygen and/or inert gas are/is added to said product gas mixture 1, and passing said product gas mixture 1, as reaction gas starting mixture 2 which comprises molecular oxygen and acrolein in a molar $O_2:C_3H_4O$ ratio of $\geq 0.5$, and at least one inert gas which comprises at least 20% by volume of molecular nitrogen, in a second reaction stage at elevated temperatures, over a second fixed-bed catalyst whose active material is at least one molybdenum- and vanadium-containing multimetal oxide, thereby obtaining a product gas mixture 2, wherein said passing of said reaction gas starting mixture 2 proceeds in such away that an acrolein conversion in a single pass is $\geq 90$ mol %, the selectivity of the acrylic acid formation balanced over both reaction stages is $\geq 80$ mol %, based on propene converted;

wherein a) a loading of said first fixed-bed catalyst with the propene contained in reaction gas starting mixture 1 is $\geq 160$ l(S.T.P.) of propene/l of catalyst bed·h, b) said first fixed-bed catalyst comprises a catalyst bed arranged in two spatially successive reaction zones A, B, wherein a temperature of reaction zone A is from 300 to 390° C. and a temperature of reaction zone B is from 305 to 420° C. and at the same time at least 5° C. above the temperature of reaction zone A, c) the reaction gas starting mixture 1 flows first through reaction zone A and then through reaction zone B, d) the reaction zone A extends to a propene conversion of from 40 to 80 mol %, e) a loading of said second fixed-bed catalyst with the acrolein contained in reaction gas starting mixture 2 is ≧140 l(S.T.P.) of acrolein/l of catalyst bed ·h, f) said second fixed-bed catalyst comprises a catalyst bed arranged in two spatially successive reaction zones C,D, wherein a temperature of reaction zone C is from 230 to 270° C. and a temperature of reaction zone D is from 250 to 300° C. and at the same time at least 5° C. above the temperature of reaction zone C, g) the reaction gas starting mixture 2 flows first through reaction zone C and then through reaction zone D, and h) the reaction zone C extends to an acrolein conversion of from 55 to 85 mol %.

2. A process as claimed in claim 1, wherein the reaction zone A extends to a propene conversion of from 50 to 70 mol %.

3. A process as claimed in claim 1, wherein the reaction zone A extends to a propene conversion of from 65 to 75 mol %.

4. A process as claimed in claim 1, wherein the reaction zone C extends to an acrolein conversion of from 65 to 80 mol %.

5. A process as claimed in claim 1, wherein the temperature of the reaction zone B is at least 10° C. above the temperature of the reaction zone A.

6. A process as claimed in claim 1, wherein the temperature of the reaction zone D is at least 20° C. above the temperature of the reaction zone C.

7. A process as claimed in claim 1, wherein the temperature of the reaction zone B is from 305 to 340° C.

8. A process as claimed in claim 1, wherein the temperature of the reaction zone B is from 310 to 330° C.

9. A process as claimed in claim 1, wherein the temperature of the reaction zone C is from 245 to 260° C.

10. A process as claimed in claim 1, wherein the temperature of the reaction zone D is from 265 to 285° C.

11. A process as claimed in claim 1, wherein the propene conversion in a single pass in the first reaction stage is ≧94 mol %.

12. A process as claimed in claim 1, wherein the selectivity of the acrolein formation and of the acrylic acid byproduct formation together in a single pass in the first reaction stage is ≧94 mol %.

13. A process as claimed in claim 1, wherein the acrolein conversion in a single pass in the second reaction stage is ≧94 mol %.

14. A process as claimed in claim 1, wherein the selectivity of the acrylic acid formation balanced over both reaction stages is ≧85 mol %, based on propene converted.

15. A process as claimed in claim 1, wherein the propene loading of the first fixed-bed catalyst is ≧165 l(S.T.P.)/l·h.

16. A process as claimed in claim 1, wherein the propene loading of the first fixed-bed catalyst is ≧170 l(S.T.P.)/l·h.

17. A process as claimed in claim 1, wherein the at least one inert gas contained in the reaction gas starting mixture 1 comprises ≧40% by volume of molecular nitrogen.

18. A process as claimed in claim 1, wherein the at least one inert gas contained in the reaction gas starting mixture 1 comprises ≧60% by volume of molecular nitrogen.

19. A process as claimed in claim 1, wherein the at least one inert gas contained in the reaction gas starting mixture 1 comprises steam.

20. A process as claimed in claim 1, wherein the at least one inert gas contained in the reaction gas starting mixture 1 comprises $CO_2$ and/or CO.

21. A process as claimed in claim 1, wherein the propene content of the reaction gas starting mixture 1 is from 4 to 15% by volume.

22. A process as claimed in claim 1, wherein the active material of the first fixed-bed catalyst is at least one multi-metal oxide of the formula I $$Mo_{12}Bi_aFe_bX^1_cX^2_dX^3_eX^4_fO_n \quad (I)$$

where $X^1$ is nickel and/or cobalt, $X^2$ is thallium, an alkali metal and/or an alkaline earth metal, $X^3$ is zinc, phosphorus, arsenic, boron, antimony, tin, cerium, lead and/or tungsten, $X^4$ is silicon, aluminum, titanium and/or zirconium, a is from 0.5 to 5, b is from 0.01 to 5, c is from 0 to 10, d is from 0 to 2, e is from 0 to 8, f is from 0 to 10 and n is a number which is determined by the valency and frequency of the elements other than oxygen in I.

23. A process as claimed in claim 1, wherein the active material of the first fixed-bed catalyst is at least one multi-metal oxide of the formula II $$[Y^1_aY^2_{b'}O_{x'}]_p[Y^3_{c'}Y^4_{d'}Y^5_{e'}Y^6_{f'}Y^7_{g'}Y^2_{h'}O_{y'}]_q \quad (II),$$

where $Y^1$ is bismuth, tellurium, antimony, tin and/or copper, $y^2$ is molybdenum and/or tungsten, $y^3$ is an alkali metal, thallium and/or samarium, $y^4$ is an alkaline earth metal, nickel, cobalt, copper, manganese, zinc, tin, cadmium and/or mercury, $y^5$ is iron, chromium, cerium and/or vanadium, $y^6$ is phosphorus, arsenic, boron and/or antimony, $y^7$ is a rare earth metal, titanium, zirconium, niobium, tantalum, rhenium, ruthenium, rhodium, silver, gold, aluminum, gallium, indium, silicon, germanium, lead, thorium and/or uranium, a' is from 0.01 to 8, b' is from 0.1 to 30, c' is from 0 to 4, d' is from 0 to 20, e' is from 0 to 20, f' is from 0 to 6, g' is from 0 to 15, h' is from 8 to 16, x',y' are numbers which are determined by the valency and frequency of the elements other than oxygen in II and p,q are numbers whose ratio p/q is from 0.1 to 10, containing three-dimensional regions which are delimited from their local environment as a result of their composition differing from their local environment and have the chemical composition $Y^1_{a'}Y^2_{b'}O_{x'}$, and whose maximum diameters are from 1 nm to 100 μm.

24. A process as claimed in claim 1, wherein the first fixed-bed catalyst comprises annular and/or spherical catalysts.

25. A process as claimed in claim 24, wherein the ring geometry is the following:

external diameter: from 2 to 10 mm, length: from 2 to 10 mm, wall thickness: from 1 to 3 mm.

26. A process as claimed in claim 24, wherein the spherical catalyst is a coated catalyst comprising a spherical support having a diameter of from 1 to 8 mm and a coat of active material applied thereon having a thickness of from 10 to 1000 μm.

27. The process as claimed in claim 1, wherein the first and the second reaction stages are each carried out in a two-zone tube-bundle reactor.

28. A process as claimed in claim 1, wherein the active material of the second fixed-bed catalyst is at least one multimetal oxide of the formula IV $$Mo_{12}V_aX^1_bX^2_cX^3_dX^4_eX^5_fX^6_gO_n \quad (IV)$$

where
- $X^1$ is W, Nb, Ta, Cr and/or Ce,
- $X^2$ is Cu, Ni, Co, Fe, Mn and/or Zn,
- $X^3$ is Sb and/or Bi,
- $X^4$ is one or more alkali metals,
- $X^5$ is one or more alkaline earth metals,
- $X^6$ is Si, Al, Ti and/or Zr,
- a is from 1 to 6,
- b is from 0.2 to 4,
- c is from 0.5 to 18,
- d is from 0 to 40,
- e is from 0 to 2,
- f is from 0 to 4,
- g is from 0 to 40 and
- n is a number which is determined by the valency and frequency of the elements other than oxygen in IV.

29. A process as claimed in claim 1, wherein the active material of the second fixed-bed catalyst is at least one multimetal oxide of the formula VI $$[D]_p[E]_q \quad (VI),$$

where
- D is $Mo_{12}V_{a''}Z^1_{b''}Z^2_{c''}Z^3_{d''}Z^4_{e''}Z^5_{f''}Z^6_{g''}O_{x''}$,
- E is $Z^7_{12}Cu_{h''}H_{i''}O_{y''}$,
- $Z^1$ is W, Nb, Ta, Cr and/or Ce,
- $Z^2$ is Cu, Ni, Co, Fe, Mn and/or Zn,
- $Z^3$ is Sb and/or Bi,
- $Z^4$ is Li, Na, K, Rb, Cs and/or H,
- $Z^5$ is Mg, Co, Sr and/or Ba,
- $Z^6$ is Si, Al, Ti and/or Zr,
- $Z^7$ is Mo, W, V, Nb and/or Ta,
- a'' is from 1 to 8,
- b'' is from 0.2 to 5,
- c'' is from 0 to 23,
- d'' is from 0 to 50,
- e'' is from 0 to 2,
- f'' is from 0 to 5,
- g'' is from 0 to 50,
- h'' is from 4 to 30,
- i'' is from 0 to 20 and
- x'',y'' are numbers which are determined by the valency and frequency of the elements other than oxygen in VI and
- p,q are numbers other than zero whose ratio p/q is from 160:1 to 1:1, which is obtainable by separately preforming a multimetal oxide material (E)

$$Z^7_{12}Cu_{h''}H_{i''}O_{y''} \quad (E)$$

in finely divided form (starting material 1) and then incorporating the preformed solid starting material 1 into an aqueous solution, an aqueous suspension or a finely divided dry blend of sources of the elements Mo, V, $Z^1$, $Z^2$, $Z^3$, $Z^4$, $Z^5$, $Z^6$, which contains the above-mentioned elements in the stoichiometry D $$Mo_{12}V_{a''}Z^1_{b''}Z^2_{c''}Z^3_{d''}Z^4_{e''}Z^5_{f''}Z^6_{g''} \quad (D)$$

(starting material 2), in the desired ratio p:q, drying any resulting aqueous mixture, and calcining the dry precursor material thus obtained, before or after it has been dried, at from 250 to 600° C. to give the desired catalyst geometry.

30. A process as claimed in claim 1, wherein the second fixed-bed catalyst comprises annular catalysts.

31. A process as claimed in claim 1, wherein the second fixed-bed catalyst comprises spherical catalysts.

* * * * *

UNITED STATES PATENT AND TRADEMARK OFFICE
CERTIFICATE OF CORRECTION

PATENT NO. : 6,998,504 B1  Page 1 of 1
DATED : February 14, 2006
INVENTOR(S) : Unverricht et al.

It is certified that error appears in the above-identified patent and that said Letters Patent is hereby corrected as shown below:

<u>Title page,</u>
Item [30], should read:
-- (30)  Foreign Application Priority Data
       Mar. 10, 1999  (DE)  ................. 199 10 506
       Mar. 10, 1999  (DE)  ................. 199 10 508
       Jun. 17, 1999  (DE)  ................. 199 27 624
       Oct. 7, 1999  (DE)  ................. 199 48 248 --.
Item [45] and [*] Notice, should read as follows:
    -- (45) Date of Patent:  * Feb. 14, 2006
    [*] Notice:  Subject to any disclaimer, the term of this patent is extended or adjusted under 35 U.S.C. 154(b) by 0 days.

This patent is subject to a terminal disclaimer. --.

Signed and Sealed this

Sixth Day of June, 2006

JON W. DUDAS
*Director of the United States Patent and Trademark Office*